United States Patent [19]

Heavner

[11] 4,250,086
[45] Feb. 10, 1981

[54] METHOD AND COMPOSITION FOR PREPARATION OF H-SAR-LYS-SAR-GLN-NH₂

[75] Inventor: George Heavner, Flemington, N.J.

[73] Assignee: Ortho Pharmaceutical Corporation, Raritan, N.J.

[21] Appl. No.: 95,744

[22] Filed: Nov. 19, 1979

Related U.S. Application Data

[63] Continuation-in-part of Ser. No. 33,641, Apr. 26, 1979.

[51] Int. Cl.³ .............................................. C07C 103/52
[52] U.S. Cl. ............................................... 260/112.5 R
[58] Field of Search ................................. 260/112.5 R

[56] References Cited

U.S. PATENT DOCUMENTS

| | | | |
|---|---|---|---|
| 3,247,180 | 4/1966 | Schwyzer et al. | 260/112.5 R |
| 3,250,760 | 5/1966 | Brenner | 260/112.5 R |
| 3,264,281 | 8/1966 | Applewhite et al. | 260/112.5 R |
| 3,300,469 | 1/1967 | Bernardi et al. | 260/112.5 R |
| 3,313,704 | 4/1967 | Li | 260/112.5 R |
| 3,317,559 | 5/1967 | Anderson | 260/112.5 R |
| 3,485,810 | 12/1969 | Tilak | 260/112.5 R |
| 3,557,077 | 9/1967 | Brunfeldt et al. | 260/112.5 R |
| 3,705,887 | 12/1972 | Wieland et al. | 260/112.5 R |
| 3,740,385 | 6/1973 | Ondetti | 260/112.5 R |
| 3,751,404 | 8/1973 | Sipos et al. | 260/112.5 R |
| 3,761,460 | 9/1973 | Pless et al. | 260/112.5 R |
| 3,761,461 | 9/1973 | Pless et al. | 260/112.5 R |
| 3,767,639 | 10/1973 | Bodanszky et al. | 260/112.5 R |

*Primary Examiner*—Delbert R. Phillips
*Attorney, Agent, or Firm*—Geoffrey G. Dellenbaugh

[57] ABSTRACT

A method for solution synthesis of H-SAR-LYS-SAR-GLN-NH₂ in good yield and compositions useful therein are disclosed.

24 Claims, No Drawings

METHOD AND COMPOSITION FOR PREPARATION OF H-SAR-LYS-SAR-GLN-NH$_2$

REFERENCE TO RELATED APPLICATION

This is a continuation-in-part of my copending application Ser. No. 33,641, filed Apr. 26, 1979.

BACKGROUND OF THE INVENTION

1. Field of the Invention

The present invention relates to methods for preparing useful peptides, and more particularly to a solution synthesis method for preparing H-SAR-LYS-SAR-GLN-NH$_2$ and compositions useful therein.

2. Description of the Prior Art

In U.S. patent application Ser. No. 960,550, filed Nov. 17, 1978, and entitled "New Tetrapeptides and Methods," a class of peptides is disclosed as being useful in thymic function and immunological areas. One of the preferred members of this class has the formula H-SAR-LYS-SAR-GLN-NH$_2$. This application is incorporated herein by reference. In the referenced application, the class of tetrapeptides was prepared by solid-phase synthesis techniques commonly described as "Merrifield Synthesis." It was also disclosed that classical techniques (i.e., solution synthetic techniques) may be employed to prepare this class of tetrapeptides. No specific classical method or synthetic route was disclosed.

While the solid-phase synthetic technique of Merrifield is a convenient one for preparation of small quantities of peptides in the laboratory, it would be impractical and generally uneconomic for preparation of large quantities (e.g., more than about 100 g) of peptide, for which solution synthesis techniques are more appropriate. Moreover, solution synthesis techniques are generally much less costly than solid phase techniques, due to the smaller amounts of reagents necessary and to the much lesser unit cost of certain of the reagents used. Among the large variety of solution synthetic techniques available for use in polypeptide preparations, Applicant has discovered a particular synthetic method which produces the desired tetrapeptide amide conveniently and economically.

SUMMARY OF THE INVENTION

The present invention in its broadest scope is a method for preparation of H-SAR-LYS-SAR-GLN-NH$_2$ which comprises the steps of:
(a) forming Fragment I, which consists of Z-SAR-εZ'-LYS-OH, as described below;
(b) forming Fragment II, which consists of H-SAR-GLN-NH$_2$, as described below;
(c) connecting Fragment I and Fragment II together to form the protected tetrapeptide;
(d) purifying the protected tetrapeptide (optional);
(e) removing the protective groups Z and Z'; and
(f) isolating and purifying the resulting tetrapeptide.

Fragment I may be formed by the steps of:
(i) protecting the α-amino group of sarcosine by allowing it to react with a reagent which will introduce the protecting group Z;
(ii) protecting the ε-amino group of L-lysine by allowing it to react with a reagent which will introduce the protecting group Z' in such a manner as to specifically protect the ε-amino group;
(iii) activating the protected sarcosine formed in step (i) with respect to nucleophilic attack at the carboxy group by an amine, to form a carboxy activated protected sarcosine, as further described below; and
(iv) reacting said carboxy activated protected sarcosine with the ε-protected L-lysine formed in step (ii), whereby Fragment I is formed.

Fragment II may be formed by the steps of:
(i) preparing Z''-GLN-NH$_2$, wherein Z'' is a protecting group on the α-amino group of the L-glutamine amide;
(ii) removing the protective group from the material prepared in step (i) above, preferably by catalytic hydrogenation, to form unprotected L-glutamine amide;
(iii) allowing the unprotected L-glutamine amide to react with the carboxy activated protected sarcosine described in step (iii) of the previous paragraph to form Z-SAR-GLN-NH$_2$; and
(iv) removing the protective group from said Z-SAR-GLN-NH$_2$, preferably by catalytic hydrogenation, whereby Fragment II is formed.

The protective groups Z and Z' may be the same or different and should be stable to removal by the steps employed for joining the amino acid groups while still being readily removable at the end of the connecting steps by conditions which will not cleave any of the amide bonds of the peptide. Protective group Z'' may be the same as or different from the groups Z and Z', and should be readily removable under conditions which will not destroy the L-glutamine amide, while being stable during the amidation of the glutamine or glutamic acid, depending upon which preparative route is used to obtain the protected L-glutamine amide. Exemplary of suitable amino-protecting groups are those of formula:

(a)

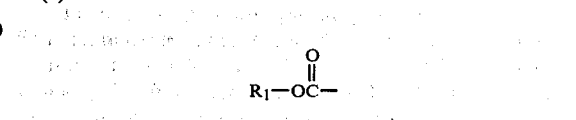

wherein R$_1$ is aryl (such as phenyl, tolyl, or xylyl); adamantyl; monosubstituted methyl (such as allyl, β-cyanoethyl, fluorenylmethyl, benzyl, or benzyl wherein the phenyl ring is substituted with from one to three members selected from halo, nitro, loweralkyl, and loweralkoxy); disubstituted methyl (such as diisopropylmethyl, diphenylmethyl, cyclohexyl, cyclopentyl, or vinyl); or trisubstituted methyl (such as t-butyl, t-amyl, dimethyltrifluoromethylmethyl, or dimethylbiphenylmethyl);

(b)

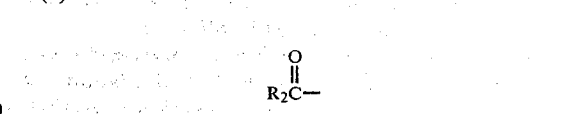

wherein R$_2$ is loweralkyl of two to four carbons such as ethyl, isopropyl, t-butyl, and the like, or loweralkyl of one to four carbons substituted with from one to five halo groups such as trifluoromethyl, chloromethyl, pentachloroethyl, and the like;

(c)

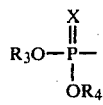

wherein X is S or O and $R_3$ and $R_4$ are each benzyl or loweralkyl;

(d)

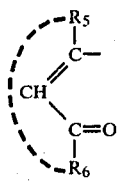

wherein $R_5$ and $R_6$ taken individually are each loweralkyl or $R_5$ and $R_6$ taken together is

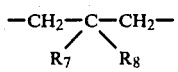

wherein $R_7$ and $R_8$ are each hydrogen or loweralkyl; and (e)

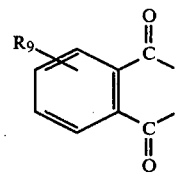

wherein $R_9$ is hydrogen, methyl, halo, or nitro.

Amino-protecting group (e), which is bidentate, may be used only for the δ-amino group of L-lysine and the α-amino group of L-glutamine, but not for the α-amino group of sarcosine. The amino-protecting group on the sarcosine α-amino must be monodentate due to the methyl substituent on that amino group. The remaining amino protecting groups may be used for all amino acids.

As used herein, "halo" includes fluoro, chloro, bromo, and iodo, but chloro and bromo are preferred. The terms "loweralkyl" and "loweralkoxy" include, respectively, saturated aliphatic hydrocarbons of one to six carbons such as methyl, ethyl isopropyl, t-butyl, n-hexyl, and the like and the corresponding alkoxies such as methoxy, ethoxy, isopropoxy, t-butoxy, n-hexoxy, and the like. Methyl is the preferred loweralkyl and methoxy is the preferred loweralkoxy.

The reagents employed to introduce these protecting groups (usually the corresponding acid chlorides, although other derivatives may be used) are sometimes referred to herein as "protecting group reagents". Other suitable protective groups are disclosed in, for example, "Protective Groups in Organic Chemistry", J. F. W. McOmie, ed., Plenum Press, N.Y., 1973.

It is preferred that Z and Z' be the same and be benzyloxycarbonyl (CBZ) or trifluoroacetyl (TFA). In a further preferred embodiment, Z, Z', and Z" are all the same and are either CBZ or TFA.

A variety of reagents may be employed for producing the carboxy activated protected sarcosine described above.

One type of carboxy activated protected sarcosine is a reactive ester. Exemplary of agents used to prepare the suitable active esters of sarcosine are phenol; phenol wherein the phenyl ring is substituted with one to five members selected from halo (e.g., chloro or fluoro), nitro, cyano, and methoxy; thiophenyl; N-hydroxyphthalimide; N-hydroxysuccinimide; N-hydroxyglutarimide; N-hydroxybenzamide; 1-hydroxybenzotriazole; and the like. Other suitable agents are disclosed in, for example, "Protective Groups in Organic Chemistry", J. F. W. McOmie, ed., referred to above. The specific examples provided below employ N-hydroxysuccinimide.

Other activation methods, such as the mixed or symmetrical anhydride method, the acid chloride method, and the azide method, are well-known in the art, being described in, e.g., Bodanszky, et al., "Peptide Synthesis", 2nd ed., 1976, pp 85-128.

As an alternative to steps (iii) and (iv) in the preparation of Fragment II, an N-carboxyanhydride of sarcosine may be employed in place of the previously described carboxy activated protected sarcosine. The preparation of N-carboxyanhydrides is generally described at pages 97 following of the Bodanszky, et al., book referred to above. This cyclic sarcosine anhydride is advantageous in the preparation of Fragment II since, due to its nature, no protection group is required on the sarcosine amino group. Thus, there is no necessity of removing the protective group, and step iv) may be eliminated. This alternate step may be described as:

(iii) allowing the unprotected L-glutamine to react with a sarcosine N-carboxyanhydride whereby Fragment II is formed.

While the protecting groups are preferably removed from the protected tetrapeptide and the Z"-GLN-NH₂ intermediate by means of catalytic hydrogenation, it is contemplated that other well-known techniques may be used. Such techniques are described at pages 18–84 of the Bodanszky, et al., book referred to elsewhere herein, as well as in the McOmie book referred to above. Exemplary of these techniques are treatment with trifluoroacetic acid or other mild acids, reduction with zinc in the presence of 50% aqueous acetic acid, treatment with hydrogen chloride or other strong acids, as well as treatment with strong or mild base, all depending on the identity of the group(s) to be removed and the other reactive groups present.

The product of the present method may be purified either in the form of the protected tetrapeptide or after removal of the protecting groups. It has been found that the protected tetrapeptide (CBZ protecting groups) may conveniently be crystallized from an ethyl acetate: methanol solvent. It is expected that other solvent systems may also be used.

While complicated purification schemes employing successive elution and recrystallization are typical in purification of solution synthesized peptides, it has surprisingly been found that the subject solution-synthesized tetrapeptide may be readily purified by a single elution on silica gel chromatography column using an eluent comprising an aliphatic alcohol, a loweralkanoic acid, and water. The aliphatic alcohol may be, for example, isobutanol, n-butanol, isopropanol, amyl alcohol, isoamyl alcohol, or the like, while the loweralkanoic acid may be formic, acetic, propionic, or the like acid.

One eluent found to work well was n-butanol:acetic acid:water in a ratio of 10:2:5.

Also included within the scope of the present invention are compositions useful for practicing the subject method, including Fragments I and II referred to above and the protected tetrapeptide, as well as intermediates for preparation of these fragments.

DETAILED DESCRIPTION OF THE INVENTION

The present method in its broadest scope is depicted diagrammatically in the following FIG. 1:

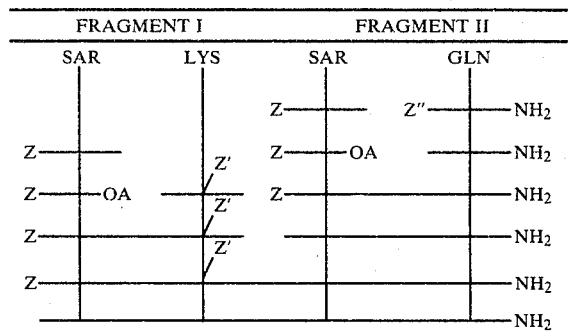

In the above Figure the protective groups are represented by Z, Z', and Z" as discussed above. The carboxy activation of sarcosine is indicated by the letters OA.

With reference to the above FIG. 1, Fragment I may generally be prepared as follows. In order to protect the amino group of sarcosine, a water-soluble basic addition salt of sarcosine is formed and dissolved in water. Conveniently, this basic addition salt can be formed by dissolving sarcosine in a slight molar excess of sodium hydroxide. To this solution is then simultaneously added a slight excess of a reagent for introducing the protecting group Z (e.g., the corresponding acid chloride such as benzyloxycarbonyl chloride) and a solution of base (e.g., sodium hydroxide) to react with the acid (e.g., HCl) formed during the reaction. The protecting group adding reagent may be in solution or neat and is preferably the acid chloride. After reaction is complete, the excess protecting group adding reagent is removed (e.g., by extraction with diethyl ether or any organic solvent immiscible with water), following which the protected sarcosine is isolated from the unreacted sarcosine by treatment with acid (e.g., hydrochloric acid). The acid treatment converts the basic addition salt of the unprotected sarcosine into an acid addition salt of the unprotected sarcosine, which salt is soluble in water. However, the acid treatment converts the protected sarcosine basic addition salt only into protected sarcosine, since no acid addition salt can be made due to the protected amino group. This protected sarcosine, being insoluble in water, is easily separated from the salt of the unprotected sarcosine, for example by extraction with an immiscible organic solvent as described above. As used herein, the term "immiscible organic solvent" includes all common laboratory organic solvents which do not mix with water, such as for example diethyl ether, ethyl acetate, benzene, toluene, xylene, and the like. The preferred protected sarcosine, N-benzyloxycarbonyl sarcosine, is a known compound. A method for its preparation is shown by R. S. Tipton and B. A. Pawson, *J. Org. Chem.*, 26, 4698 (1961), and the compound is commercially available from Bachem, Inc., Torrance, CA.

In preparation for the condensation of this protected sarcosine with a protected L-lysine molecule to form Fragment I, the amino-protected sarcosine should usually be activated in some fashion to promote the formation of the bond. While the preferred way of conducting this activation is by formation of "active ester", it is contemplated that other methods of activation known in the art such as the mixed or symmetrical anhydride, azide, or acid chloride methods could be employed. Additionally, if the carboxyl end of the $N^\epsilon$-protected L-lysine is blocked by a group which is removable in the presence of the protecting group on the sarcosine (Z) without removing either Z or the $N^\epsilon$-protecting group on the L-lysine (Z'), such blocking will allow direct coupling of the protected sarcosine to the L-lysine without prior activation of the sarcosine.

It is contemplated that any active ester of the protected sarcosine could be employed; one preferred active ester is that formed by hydroxysuccinimide. The active ester of the protected sarcosine is prepared by reacting equivalent quantities of the protected sarcosine and an active ester reagent in solution of a suitable organic solvent such as, for example, tetrahydrofuran, dioxane, dimethylformamide, pyridine, or the like. To this solution is then added an equivalent amount of a coupling agent, typically dicyclohexylcarbodiimide. While other coupling agents are effective, dicyclohexylcarbodiimide is particularly useful because the by-product of the coupling reaction is very insoluble in the class of solvents used, and therefore may easily be removed by filtration, leaving the coupled product in solution.

L-lysine which is protected on its epsilon-amino group is commercially available (e.g., from Sigma Chemical Company, St. Louis, MO) or may be prepared with a protecting group (Z') meeting the criteria set forth above.

The final step in the preparation of Fragment I consists of reacting a slight excess of the protected L-lysine with the protected sarcosine active ester in the presence of two equivalents of a salt-forming material such as an organic tertiary amine. While any organic tertiary amine may be used, triethylamine has been found to work well. The solvent is an suitable organic solvent as described above. Although one equivalent of the salt-forming tertiary amine protects the carboxyl group of the epsilon-amino protected L-lysine, it is contemplated that other protective groups on this carboxyl group could also be used in place of one of the equivalents referred to above. The unreacted amino acids are removed by treatment of the reaction mixture with acid (e.g., hydrochloric acid) and separation by extraction with an immiscible organic solvent as described above.

Exemplary of suitable carboxyl protecting groups are benzyl and benzyl in which the phenyl group is substituted with from one to three members of halo (e.g., chloro or bromo), nitro, loweralkoxy (e.g., methoxy), or loweralkyl (e.g., methyl). See the above-referenced McOmie text for further description of such groups.

The preparation of Fragment II begins with the synthesis of protected L-glutamine amide, which may be obtained by one of several preparative routes starting with either L-glutamine or L-glutamic acid. The preferred method is to esterify both carboxyl groups of L-glutamic acid using a loweralkanol, followed by treatment with the amino group protecting reagent as described above to protect the alpha-amino group of the L-glutamic acid diester. Reaction of this protected L-glutamic acid diester with ammonia affords the protected L-glutamine amide. This method is disclosed in *J. Biol. Chem.*, 165, 333 (1946). In a variation of this method, the alpha-amino group of the L-glutamic acid may be protected prior to the esterification reaction. An alternate procedure, which is novel, begins with L-glutamine and protects the alpha-amino group thereof as previously discussed. The protected L-glutamine is then converted to the protected L-glutamine amide, for example by formation of an active ester followed by treatment with ammonia in a loweralkanol (e.g., methyl alcohol).

Once this protected L-glutamine amide is produced, the protecting group is removed from the alpha-amino group and the unprotected L-glutamine amide is reacted with alpha-amino protected sarcosine which has been activated (e.g., by conversion into an active ester) as discussed above. The deprotection of the L-glutamine amide is preferably conducted by reaction with hydrogen in the presence of a palladium on carbon catalyst in a suitable reducing solvent such as dimethylformamide, acetic acid, a loweralkanol (e.g., methanol), or the like. The reaction of the resulting deprotected L-glutamine amide with the protected sarcosine active ester is also preferably conducted in the same solvent, preferably methanol. The use of this particular method of deprotection and solvent results in particular advantages, since both the protected L-glutamine amide and the resulting protected sarcosine-L-glutamine amide are insoluble in methyl alcohol, while the deprotected L-glutamine amide is quite soluble in methyl alcohol. Consequently, the deprotected L-glutamine amide which is unreacted can easily be removed by filtration,
as can the resulting product, resulting in an excellent yield for this step.

Removal of the protecting group from this protected dipeptide, conveniently by treatment with hydrogen and palladium on carbon in a suitable reducing solvent as described above (preferably dimethylformamide) yields Fragment II.

Fragments I and II are joined to form the protected tetrapeptide Z-Sar-ε-Z'-LYS-SAR-GLN-NH$_2$ by reacting equivalent amounts in a suitable aprotic solvent such a dimethylformamide in the presence of a slight excess of a coupling agent such as dicyclohexylcarbodiimide.

It is also preferred to conduct this reaction in the presence of a material which minimizes racemization adjacent to the carboxyl group on the L-lysine portion of Fragment I and enhances the rate of reaction, such as for example 1-hydroxybenzotriazole. The remaining groups on the resulting tetrapeptide amide are then removed, preferably by treatment with hydrogen gas in the presence of a palladium on carbon catalyst in a suitable reducing solvent as described above (preferably aqueous acetic acid). The hydrogen gas need not be under a pressure greater than one atmosphere, although the use of pressure is convenient since it accelerates the rate of reduction.

The isolation and purification of the resulting impure product may be accomplished by a combination of crystallization and ion exchange chromatography, (preferably using ammonium acetate-pH5 as eluent) using thin-layer chromatography to monitor the identity of the materials in each fraction. While several isolation and purification procedures are given in the following examples, it is clearly contemplated that others could be used.

The protected tetrapeptide produced above may be purified prior to the reduction step, if desired. This purification may be accomplished by removing the solvent from the solution of protected tetrapeptide, dissolving the residue in dichloromethane, filtering the solution, and evaporating the filtrate. Extraction of the resulting solid with hot ethyl acetate yields the pure protected tetrapeptide, which may be reduced and further purified as described above. Alternatively, the impure protected tetrapeptide may be purified by recrystallization from a suitable solvent system (e.g., ethyl acetate:methanol in a 10:1 ratio).

One preferred embodiment of the present method is depicted by the following FIG. 2:

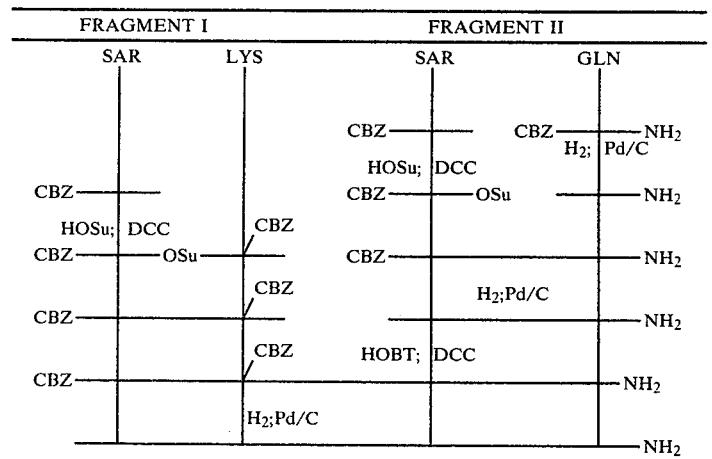

In the above FIG. 2 the abbreviations have the following meaning:
CBZ: Benzyloxycarbonyl
DCC: Dicyclohexylcarbodiimide
HOSu: Hydroxysuccinimide
OSu: Oxysuccinimide
Pd/C: Palladium on Carbon
H$_2$: Hydrogen
HOBT: 1-Hydroxybenzotriazole This preferred embodiment is described in greater detail in the following examples, which will serve to illustrate the present invention.

EXAMPLE I

Preparation of Fragment I: CBZ-SAR-ε-CBZ-LYS-OH

A. Synthesis of N-phenylmethoxycarbonyl-sarcosine (CBZ-SAR-OH)

This material was prepared following the method of R. S. Tipton and B. A. Pawson [*J. Org. Chem.*, 26, 4648 (1961)]. Sarcosine (8.90 g, 1.0 mole) was dissolved in 500 ml of 2 N sodium hydroxide with cooling in an ice bath. Simultaneously, 550 ml of 2 N sodium hydroxide and benzyl chloroformate [196 g (95%), 1.095 moles] were added over a period of one hour with rapid stirring. The resulting reaction mixture was stirred for about 18 hours at ambient temperature, after which time it was extracted with three 250 ml portions of diethyl ether. Ethyl acetate (500 ml) was then added to the aqueous phase, followed by the careful addition of 200 ml of concentrated hydrochloric acid. The organic layer was separated, washed with two 500 ml portions of water followed by 300 ml of saturated sodium chloride solution, and dried over anhydrous magnesium sulfate. Evaporation of the solvent under reduced pressure after removal of the drying agent by filtration gave 213 g (95%) of N-phenylmethoxycarbonyl-sarcosine as an oil which was identified by nmr spectroscope and used without further purification.

nmr (CDCl$_3$)δ: 3.02(S,3H,—N—C$\underline{H}_3$), 4.05(Broad,2-H,—N—C$\underline{H}_2$), 5.15(S,2H,benzyl), 7.35(S,5H,aromatic), 10.4(S,1H,acid).

B. Synthesis of N-phenylmethoxycarbonyl-sarcosine N-hydroxysuccinimide ester (CBZ-SAR-OSu)

N-Phenylmethoxycarbonyl-sarcosine prepared in Example IA (146 g, 0.6547 moles) and N-hydroxysuccinimide [77.6 g (97%), 0.6547 moles] were dissolved in 1500 ml of dry tetrahydrofuran with cooling in an ice bath. To this solution was added with rapid stirring and cooling a solution of dicyclohexylcarbodiimide (134.9 g, 0.6547 mole) in 500 ml of dry tetrahydrofuran. The resulting solution was stirred for about 18 hours at room temperature. The solid was removed by filtration, and the solvent evaporated under reduced pressure to yield an oil, which was crystallized from two liters of absolute ethanol to give 160 g (76.3%) of N-phenylmethoxycarbonyl-sarcosine N-hydroxysuccinimide ester as a white solid; m.p. 69-78° C.

nmr (CDCl$_3$)δ: 2.7(S,4H,—C$\underline{H}_2$—C$\underline{H}_2$—), 2.06(S,3H,—N—C$\underline{H}_3$), 4.3(S,2H—N—C$\underline{H}_2$), 5.08(S,2H,benzyl), 7.3(S,5H, aromatic; ir(KBr): 2940-3070 cm$^{-1}$ (aliphatic and aromatic. C—H), 1830 cm$^{-1}$ (imide):

Anal. Calcd for C$_{15}$H$_{10}$N$_2$O$_6$: C, 56.25; H, 5.03; N, 8.75; Found: C, 55.93; H, 5.06; N, 8.85.

C. Synthesis of N-phenylmethoxycarbonyl-sarcosyl-N$^\epsilon$ phenylmethoxycarbonyl-L-lysine (CBZ-SAR-ε-CBZ-LYS-OH)

N-Phenylmethoxycarbonyl-sarcosine-N-hydroxysuccinimide ester from Example IB (25 g, 0.0744 moles), N$^\epsilon$-phenylmethoxycarbonyl-L-lysine (purchased from Sigma Chemical Company, St. Louis, MO) (22 g, 0.0786 moles), and triethylamine (22 ml, 16 g, 0.158 moles) were added to 450 ml of dry tetrahydrofuran and the whole stirred for about 18 hours at room temperature. The solvent was removed under reduced pressure and the residue was partitioned between 500 ml of ethyl acetate and 400 ml of 2 N hydrochloric acid. The aqueous layer was separated and extracted with 100 ml of ethyl acetate. The combined ethyl acetate fractions were then washed with two 200 ml portions of 2 N hydrochloric acid, 200 ml of water and twice with 200 ml of saturated sodium chloride solution, followed by drying over anhydrous magnesium sulfate. After removal of the drying agent by filtration, the solvent was removed from the solution under reduced pressure and the residue was triturated with 900 ml acetone hexane (1:3) to give 29.9 g (82.8%) of N-phenylmethoxycarbonyl-sarcosyl-N$^\epsilon$-phenylmethoxycarbonyl-L-lysine as a white solid. Alternately, recrystallization of the untriturated solid from 500 ml toluene yielded pure product.

nmr (TFA)C: 1.3-2.2 (M,6H,C—C$\underline{H}_2$—C$\underline{H}_2$—C of lysine), 3.08(S+M,5H,—N—C$\underline{H}_2$—of lysine and C$\underline{H}_3$—N—of sarcosine),

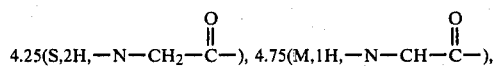

5.2(S,4H,benzyl), 7.3(S+M,12H,aromatic+—N–H),
ir(KBr): 3330 cm$^{-1}$ (amide N—H), 1650-1750 cm$^{-1}$, amide, (acid and urethane C=O). (α)$_p^{19.9}$=2° (C=1.00, HOAc)

Anal. Calcd for C$_{25}$H$_{31}$N$_3$C$_7$: C, 61.84; H, 6.44; N, 8.65; Found: C, 61.03; H, 6.47; N, 8.61.

EXAMPLE II

Preparation of Fragment II: H-SAR-GLN-NH$_2$

A. Synthesis of N-phenylmethoxycarbonyl-L-glutamine amide (CBZ-GLN-NH$_2$)

L-Glutamic acid (44 g, 0.3 moles) was suspended in 250 ml of absolute methanol and the suspension was heated under reflux for 0.5 hours while dry HCl gas was bubbled through the suspension, at the end of which time all material had gone into solution. The solution was heated under reflux for a further period of about 18 hours, following which the solvent was evaporated under reduced pressure. To the resulting residue was added 200 ml of water and 300 ml of chloroform, and the resulting mixture was stirred rapidly at room temperature while 5 g of magnesium oxide and 18 g of benzyl chloroformate were added, following which the rapid stirring was continued for an additional ten minutes. This addition followed by a ten minute stirring period was repeated three subsequent times to give a total added amount of (20 g, 0.496 moles) of magnesium oxide and (72 g, 0.423 moles) of benzyl chloroformate. After the final addition, the reaction mixture was stirred for 15 minutes rather than ten minutes. The organic layer was separated and washed with two 200 ml portions of water, two 200 ml portions of 0.5 N hydrochloric acid, two further 200 ml portions of water, two 200 ml portions of 0.5 N sodium hydroxide, and two final 200 ml portions of water, and dried over anhydrous magnesium sulfate.

The drying agent was removed by filtrating and the solvent removed under reduced pressure. The residual oil was dissolved in methanol (500 ml) which had been previously saturated with ammonia and let stand at room temperature for six days. The resulting solid was removed by filtration and recrystallized from EtOH to give a white solid, (19.35 g, 23%) m.p. 189°-195° C.

nmr (CH$_3$CO$_2$D)δ: 4.3(M,1H,methyne), 5.1(s,2H,benzyl), 7.3(S,5H,aromatic).

ir(KBr): 3440 cm$^{-1}$, 3320 cm$^{-1}$ and 3200 cm$^{-1}$ (Amide and urethane N—H), 1650 cm$^{-1}$ (amide) 1540 cm$^{-1}$ (amide). $(\alpha)_D^{22.4°} = +6°$ (c=2.012, DMF)

Anal. Calcd for $C_{13}H_{17}N_3O_4$: C, 55.91; H, 6.14; N, 15.04; Found: C, 56.76; H, 6.24; N, 14.88.

Alternate Methods for Synthesis of CBZ-GLN-NH-hd 2

(1) To a cooled solution of 8.41 g (30 mmole) of benzyloxycarbonyl-L-glutamine and 3.45 g (30 mmole) of hydroxysuccinimide in 100 ml of tetrahydrofuran was added 6.18 g (30 mmole) of dicyclohexylcarbodiimide with stirring. The whole was stirred for 18 hours and allowed to come to ambient temperature. The solution was filtered, the filtrate evaporated to dryness, and the residue recrystallized from ethyl acetate. The resulting solid was then dissolved with heating in 75 ml of methanol saturated with ammonia and allowed to stand at ambient temperature for 18 hours. The resulting solid was filtered off, washed with cold methanol and twice recrystalized from 95% ethanol to yield 1.8 g of solid; m.p. 191.5°–195.5° C. The nmr spectrum, ir spectrum, optical rotation, and elemental analysis confirmed the identity and purity of the product.

(2) A suspension of 220 g (1.495 moles) of L-glutamic acid in 1250 ml of absolute methanol was heated to reflux and hydrogen chloride was bubbled through it for seven hours until solution was effected. The solution was heated under reflux for a further 18 hours, after which it was evaporated under reduced pressure to yield the hydrochloride salt of L-glutamic acid. The hydrochloride salt was dissolved in one liter of deionized water and 1.5 l of chloroform was added. To this solution was then added 360 g (2.11 moles) of benzyloxycarbonyl chloride and 120 g (3 moles) of magnesum oxide over a 1.25 hour interval with stirring and the stirring continued for a further half hour. The whole was filtered to remove any undissolved magnesium oxide and the organic layer of the filtrate separated. The organic layer was washed twice with 1.0 l of deionized water, twice with 1.0 l of 0.5 N aqueous sodium hydroxide, and finally four times with 1.0 l of deionized water. The washed organic layer was dried over magnesium sulfate, filtered, and evaporated to dryness to yield 500 g of crude solid. This crude solid was dissolved in a mixture of 2.0 l of methanol and 500 ml of ammonium hydroxide, allowed to stand at ambient temperature for ten days and then refrigerated for three days. The resulting solid was filtered off, washed with methanol, dried under vacuum, and recrystallized from 15 l of isopropanol to yield 198 g of pure product. The identity and purity of the product were confirmed by nmr and ir spectra, optical rotation, and elemental analysis.

B. Synthesis of N-phenylmethoxycarbonyl-sarcosyl-L-glutamine amide (CBZ-SAR-GLN-NH$_2$)

N-Phenylmethoxycarbonyl-L-glutamine amide prepared in Example IIA (13.6 g, 0.0473 moles) was suspended in 300 ml of methanol. To this suspension was added palladium on carbon (10%, 1.1 g) and the suspension was shaken under 45 psi of hydrogen. After 0.5 hours the hydrogen uptake was 4.5 psi, corresponding to approximately 0.05 moles of hydrogen. The catalyst was removed by filtration and washed with 50 ml of methanol. To the combined methanol solutions was added N-phenylmethoxycarbonyl-sarcosine-N-hydroxy-succinimide ester prepared in Example IB (19.36 g, 0.0605 moles) and the reaction mixture was stirred for about 18 hours at room temperature. The resulting solid was removed by filtration, washed with methanol, and dried, yielding 14.9 g (90%) of N-phenyl-methoxycarbonyl-sarcosyl-L-glutamine amide; m.p. 186°–196° C.

nmr (CD$_3$CO$_2$D)ϵ: 2.3(M,1H,—C$\underline{H}_2$—C$\underline{H}_2$ of glutamine), 3.0(S,3H,—N—C$\underline{H}_3$),

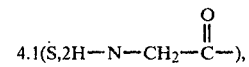

4.1(S,2H—N—CH$_2$—C̈—), 4.6(M, 1H,—N—C$\underline{H}$—C—), 5.15(S,2H,benzyl), 7.3(S,5H,aromatic)

ir(KBr): 3410 cm$^{-1}$, 3290 cm$^{-1}$ and 3220 cm$^{-1}$ and 3220 cm$^{-1}$. (amide and urethane —N—H), 1700 cm$^{-1}$ (urethane carbonyl), 1650 cm$^{-1}$ and 1625 cm$^{-1}$ (amide carbonyls). $(\alpha)_D^{22.6°} = +23.3°$ (C=1.032, DMF).

Anal. Calcd for $C_{10}H_{22}N_4O_5$: C, 54.85; H, 6.33; N, 15.99; Found: C, 54.62; H, 6.23; N, 15.56.

C. Synthesis of Sarcosyl-L-lysyl-sarcosyl-L-glutamine amide (H-SAR-LYS-SAR-GLN-NH$_2$)

N-Phenylmethoxycarbonyl-sarcosyl-L-glutamine amide (17.4 g, 0.0497 moles) as prepared in Example IIB was suspended in 370 ml of dimethylformamide along with 2 g of 10% Pd/C and hydrogen gas was bubbled through the solution for six hours. After the catalyst was removed by filtration, 1-hydroxybenzotriazole (13.4 g, 0.10 moles) and N-phenylmethoxycarbonyl-sarcosyl-N$^\epsilon$-phenylmethoxycarbonyl-L-lysine (24 g, 0.0497 moles) as prepared in Example ID were added to the filtrate and the resulting solution was cooled in an ice bath. Dicyclohexylcarbodiimide (10.24 grams, 0.0505 moles) was then added, and the resulting mixture was stirred overnight without cooling, so that the temperature of the mixture gradually reached ambient temperature.

The suspension was filtered and the solvent removed from the filtrate under reduced pressure. The residue from the filtrate was dissolved in methylene chloride, cooled to −20° C. for 18 hours, filtered, and the filtrate evaporated under reduced pressure to yield the amino-blocked tetrapeptide amide.

This material was then dissolved in 300 ml of 50% aqueous acetic acid and reduced under 40 psi of hydrogen in the presence of 2.5 g of 10% Pd/C. After 2.5 hours the uptake of hydrogen was approximately six psi. After the catalyst had been removed by filtration, the filtrate was lyopholyzed to yield the impure product, which was purified as follows.

The impure solid was chromatographed on a 5×80 centimeter chromatography column of SP-C-25 resin which had been packed in 0.5 M ammonium acetate (pH 6.50) (void volume 560 ml) and eluted with a linear gradient of two liters of 0.5 M ammonium acetate (pH 6.50) and two liters of 0.8 M ammonium acetate (pH 6.50). The flow rate was 150 ml/hr and 15 ml fractions were collected. Fractions numbers 160–200 were pooled and lyophilyzed, following which the resulting solid was rechromatographed under the same conditions as above and fractions numbers 81–320 were pooled and lyophilyzed.

The resulting product was then chromatographed on a partition column of G-25 resin fine packed in the lower phase of a 4:1:5 mixture of n-butanol, acetic acid, and water, and eluted with the upper phase of this mixture. The column size was 5×85 cm, the flow rate was 100 ml/hr, and 20 ml fractions were collected. Fractions numbers 51–240, 241–340, and 341–520 were separately pooled and evaporated to yield 4 g, 5.4 g, and 3.8 g of product, respectively. Each of these three products was rechromatographed separately on the partition column described above and the resulting fractions were monitored by thin-layer chromatography (TLC) using silica gel plates and a solvent system consisting of 4:2:3:1 n-butanol/acetic/acid/water/pyridine. Those fractions containing pure product (about numbers 340-420) for each of the three products obtained above were pooled together and evaporated.

The resulting resulting residue was dissolved in 500 ml of absolute ethyl alcohol, precipitated by addition of 100 ml of absolute ethyl alcohol saturated with hydrogen chloride gas, and treated with 500 ml of anhydrous ether. The resulting solid was filtered, washed with ether, and dried under reduced pressure to give 7.81 g of sarcosyl-L-lysyl-sarcosyl-L-glutamine amide dihydrochloride as a white solid.

| TLC: (Silica gel plates) | | |
|---|---|---|
| Solvent | | $R_f$ |
| N-Butanol/HOAc/H$_2$O/pyridine | 4/2/3/1 | 0.48 |
| CHCl$_3$/MeOH/NH$_4$OH (conc) | 30/25/10 | 0.42 |
| N-Butanol/HOAc/h$_2$O/pyridine | 15/3/12/10 | 0.27 |
| N-Butanol/NOAc/EtOAc/H$_2$O | 1/1/1/1 | 0.12 |
| N-Butanol/HOAc/H$_2$O (upper) | 4/1/5 | 0.02 |
| Amino Acid Analysis: | Sar (2.19), Glu (1.03), Lys (1.00)$^\pm$, NH$_3$ (2.01), 80.4% peptide. | |
| Analysis: Cl$^-$: | 14.89%; H$_2$O: 4.92% | |

$(\alpha)_D^{22.4} = -14.8°$ (C = 0.2022, 0.1 N HCl).

Alternate methods of purification include reverse phase high performance liquid chromatography using an alkyl silane substate. The simplest purification method found involved chromatography on silica gel with an eluent comprising an aliphatic alcohol, a lower alkanoic acid (including formic acid) and water as described above. The preferred n-butanol:acetic acid:warter (10:2:5) eluent was used to purify 10 g of impure tetrapeptide on a 100 g column of Malenkrodt Silicar CC7 silica gel. Fifteen ml fractions were taken. Fractions 50-95 were found to contain pure tetrapeptide as determined by TLC on silica gel plate using chloroform:methanol:ammonium hydroxide in a 30:25:10 ratio-eluent and developing with ninhydrin.

The tetrapeptide may be obtained in pure form by recrystallizing the protected tetrapeptide prior to removal of the protecting groups. A 28 g sample of the impure protected tetrapeptide was purified by recrystallization from a mixture of 600 ml ethyl acetate and 70 ml methanol. The product was essentially pure by TLC (chloroform:methanol; 9:1, $R_f$=0.72) and elemental analysis. The nmr spectrum was consistent with the assigned structure.

EXAMPLE III

The pure H-SAR-LYS-SAR-GLN-NH$_2$ produced in Example IIC above was tested in the mouse induction assay described in Example II of U.S. patent application Ser. No. 960,550, filed Nov. 17, 1978, referred to above. This tetrapeptide amide prepared as described in Examples I and II above exhibited the same activity as the material prepared according to the Merrifield solid-phase synthesis technique.

What is claimed is:

1. The dipeptide of formula Z-SAR-$\epsilon$-Z'-LYS-OH, wherein Z and Z' are each selected from the group consisting of (a)

wherein R$_1$ ia phenyl; tolyl; xylyl; adamantyl; allyl; $\beta$-cyanoethyl; fluorenylmethyl; benzyl, benzyl wherein the phenyl ring is substituted with from one to three members selected from halo, nitro, loweralkyl, and loweralkoxy; diisopropylmethyl; diphenylmethyl; cyclohexyl; cyclopentyl; vinyl; t-butyl; t-amyl; dimethyltrifluoromethylmethyl; or dimethylbiphenylmethyl;

(b)

wherein R$_2$ is loweralkyl of two to four carbons or loweralkyl of one to four carbons substituted with from one to five halo groups;

(c)

wherein X is S or O and R$_3$ and R$_4$ are each benzyl or loweralkyl;

(d)

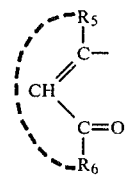

wherein R$_5$ and R$_6$ taken individually are each loweralkyl or R$_5$ and R$_6$ taken together is

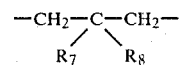

wherein R$_7$ and R$_8$ are each hydrogen or loweralkyl; and (e)

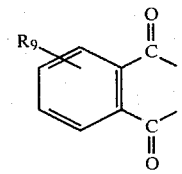

wherein R$_9$ is hydrogen, methyl, halo, or nitro provided that Z is monodentate.

2. The dipeptide of claim 1 wherein Z and Z' are the same.

3. The dipeptide of claim 2 wherein Z and Z' are each benzyloxycarbonyl or trifluoroacetyl.

4. The dipeptide of formula H-SAR-GLN-NH$_2$.

5. The tetrapeptide of formula Z-SAR-$\epsilon$-Z'-LYS-SAR-GLN-NH$_2$, wherein Z and Z' are each selected from the group consisting of (a)

wherein R$_1$ is phenyl; tolyl; xylyl; adamantyl; allyl; $\beta$-cyanoethyl; fluorenylmethyl; benzyl; benzyl wherein the phenyl ring is substituted with from one to three members selected from halo, nitro, loweralkyl, and loweralkoxy; diisopropylmethyl; diphenylmethyl; cyclohexyl; cyclopentyl; vinyl; t-butyl; t-amyl; dimethyltrifluoromethylmethyl; or dimethylbiphenylmethyl;

(b)

wherein R$_2$ is loweralkyl of two to four carbons or loweralkyl of one to four carbons substituted with from one to five halo groups;

(c)

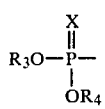

wherein X is S or O and R$_3$ and R$_4$ are each benzyl or loweralkyl;

(d)

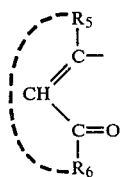

wherein R$_5$ and R$_6$ taken individually are each loweralkyl or R$_5$ and R$_6$ taken together is

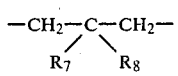

wherein R$_7$ and R$_8$ are each hydrogen or loweralkyl; and (e)

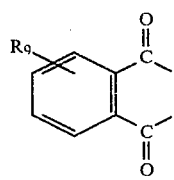

wherein R$_9$ is hydrogen, methyl, halo, or nitro provided that Z is monodentate.

6. The tetrapeptide of claim 5 wherein Z and Z' are the same.

7. The tetrapeptide of claim 6 wherein Z and Z' are each benzyloxycarbonyl or trifluoroacetyl.

8. A method for preparation of the peptide H-SAR-LYS-SAR-GLN-NH$_2$ which comprises:

(a) forming Fragment I, which consists of Z-SAR-$\epsilon$-Z'-LYS-OH, by:
  (i) protecting the amino group of sarcosine by allowing it to react with a reagent which will introduce the protecting group Z;
  (ii) protecting the $\epsilon$-amino group of L-lysine by allowing it to react with a reagent which will introduce the protecting group Z' in such a manner as to specifically protect to $\epsilon$-amino group;
  (iii) activating the protected sarcosine formed in step (i) with respect to nucleophilic attack at the carboxy group by an amine to form a carboxy activated protected sarcosine; and
  (iv) allowing said carboxy activated protected sarcosine to react with the $\epsilon$-protected L-lysine formed in step (a) (ii) above, whereby Fragment I is formed.

(b) forming Fragment II, which consists of H-SAR-GLN-NH$_2$, by:
  (i) preparing Z''-GLN-NH$_2$;
  (ii) removing the protective group from said Z''-GLN-NH$_2$ to form unprotected L-glutamine amide;
  (iii) allowing the unprotected L-glutamine amide to react with the carboxy activated protected sarcosine formed in step (a) (iii) above to form Z-SAR-GLN-NH$_2$; and
  (iv) removing the protective group from said Z-SAR-GLN-NH$_2$ whereby Fragment II is formed.

(c) connecting Fragment I and Fragment II together to form the protected tetrapeptide Z-SAR-$\epsilon$-Z'-LYS-SAR-GLN-NH$_2$;

(d) removing the protective groups from said protected tetrapeptide; and (e) isolating and purifying the resulting tetrapeptide H-SAR-LYS-SAR-GLN-NH$_2$;

wherein Z, Z', and Z'' are each selected from the group consisting of:

(a)

wherein R$_1$ is phenyl; tolyl; xylyl; adamantyl; allyl; $\beta$-cyanoethyl; fluorenylmethyl; benzyl; benzyl wherein the phenyl ring is substituted with from one to three members selected from halo, nitro, loweralkyl, and loweralkoxy; diisopropylmethyl; diphenylmethyl; cyclohexyl; cyclopentyl; vinyl; t-butyl; t-amyl; dimethyltrifluoromethylmethyl; or dimethylbiphenylmethyl;

(b)

wherein R$_2$ is loweralkyl of two to four carbons or loweralkyl of one to four carbons substituted with from one to five halo groups;

(c)

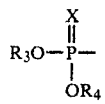

wherein X is S or O and $R_3$ and $R_4$ are each benzyl or loweralkyl;

(d)

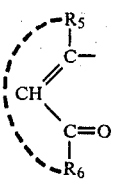

wherein $R_5$ and $R_6$ taken individually are each loweralkyl or $R_5$ and $R_6$ taken together is

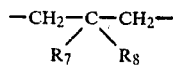

wherein $R_7$ and $R_8$ are each hydrogen or loweralkyl; and (e)

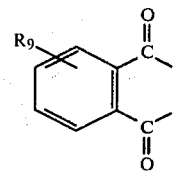

wherein $R_9$ is hydrogen, methyl, halo, or nitro provided that Z is monodentate.

9. The method of claim 8 wherein Z, Z' and Z" are the same.

10. The method of claim 9 wherein Z, Z' and Z" are each benzyloxycarbonyl or each trifluoroacetyl.

11. The method of claim 8 wherein the carboxy activated protected sarcosine formed in step (a) (iii) is a reactive ester of protected sarcosine.

12. The method of claim 8 wherein the protective groups are removed by catalytic hydrogenation in steps (b) (ii), (b) (iv), and (d).

13. A method for the preparation of the peptide H-SAR-LYS-SAR-GLN-$NH_2$ which comprises:

(a) forming Fragment I, which consists of CBZ-SAR-ϵ-CBZ-LYS-OH, by:
(i) esterifying CBZ-SAR-OH by allowing it to react with an equivalent amount of N-hydroxysuccinimide in the presence of dicyclohexylcarbodiimide to form CBZ-SAR-OSu; and
(ii) allowing a slight molar excess CBZ$^ϵ$-LYS-OH to react with CBZ-SAR-OSu in the presence of two equivalents of triethylamine to form CBZ-SAR-ϵCBZ-LYS-OH (Fragment I).

(b) forming Fragment II, which consists of H-SAR-GLN-$NH_2$, by:
(i) preparing CBZ-GLN-$NH_2$;
(ii) removing the benzyloxycarbonyl group by catalytic hydrogenation to form H-GLN-$NH_2$;
(iii) allowing GLN-$NH_2$ to react with a molar excess of CBZ-SAR-OSu to form CBZ-SAR-GLN-$NH_2$; and
(iv) removing the benzyloxycarbonyl group by catalytic hydrogenation to form H-SAR-GLN-$NH_2$ (Fragment II).

(c) connecting the carboxyl terminus of Fragment I to the amino terminus of Fragment II by mixing equivalent amounts of each fragment in the presence of 1-hydroxybenzotriazole and a slight molar excess of dicyclohexylcarbodiimide;

(d) removing the benzyloxycarbonyl groups by catalytic hydrogenation to yield crude product; and (e) isolating and purifying the resulting tetrapeptide H-SAR-LYS-SAR-GLN-$NH_2$.

14. The method of claim 13 wherein the purification of the resulting tetrapeptide in step (e) comprises chromatographing the crude product on a silica gel chromatography column with an eluent consisting essentially of an aliphatic alcohol, a loweralkanoic acid and water in proportions effective to yield essentially pure tetrapeptide H-SAR-LYS-SAR-GLN-$NH_2$.

15. The method of claim 14 wherein the eluent is n-butanol:acetic acid:water in ratio of 10:2:5.

16. The method of claim 13 which comprises the additional step of purifying by recrystallization the protected tetrapeptide obtained in step (c).

17. The method of claim 16 wherein the protected tetrapeptide is recrystallized from a solvent consisting essentially of ethyl acetate and methanol in a ratio of about 10:1.

18. The method of claim 13 wherein the preparation of CBZ-GLN-$NH_2$ in substep (b) (i) comprises the steps of:

(a) esterifying both carboxyl groups of L-glutamic acid with a loweralkanol to produce L-glutamic acid diester;
(b) allowing the L-glutamic acid diester to react with benzyloxycarbonyl chloride to produce CBZ-GLU diester; and
(c) allowing the CBZ-GLU diester to react with ammonia in a loweralkanol to produce CBZ-GLN-$NH_2$.

19. The method of claim 13 wherein the preparation of CBZ-GLN-$NH_2$ in substep (b) (i) comprises the steps of:

(a) allowing L-glutamine to react with benzyloxycarbonyl chloride to produce CBZ-GLN;
(b) allowing the CBZ-GLN to react with hydroxysuccinimide to form CBZ-GLN-OSu; and
(c) treating the CBZ-GLN-OSu with ammonia in a loweralkanol to produce CBZ-GLN-$NH_2$.

20. A method for preparation of the peptide H-SAR-LYS-SAR-GLN-$NH_2$ which comprises:

(a) forming Fragment I, which consists of Z-SAR-ϵ-Z'-LYS-OH, by:
(i) protecting the amino group of sarcosine by allowing it to react with a reagent which will introduce the protecting group Z;
(ii) protecting the ϵ-amino group of L-lysine by allowing it to react with a reagent which will introduce the protecting group Z' in such a manner as to specifically protect to ϵ-amino group;
(iii) activating the protected sarcosine formed in step (i) with respect to nucleophilic attack at the carboxy group by an amine to form a carboxy activated protected sarcosine; and (iv) allowing said carboxy activated protected sarcosine to react with the ε-protected L-lysine formed in step (a) (ii) above, whereby Fragment I is formed.
(b) forming Fragment II, which consists of H-SAR-GLN-NH$_2$, by:
  (i) preparing Z''-GLN-NH$_2$;
  (ii) removing the protective group from said Z''-GLN-NH$_2$ to form unprotected L-glutamine amide;
  (iii) allowing the unprotected L-glutamine amide to react with a sarcosine N-carboxyanhydride, whereby Fragment II is formed.
(c) connecting Fragment I and Fragment II together to form the protected tetrapeptide Z-SAR-ε-Z'-LYS-SAR-GLN-NH$_2$;
(d) removing the protective groups from the protected tetrapeptide; and
(e) isolating and purifying the resulting tetrapeptide H-SAR-LYS-SAR-GLN-NH$_2$;

wherein Z, Z', and Z'' are each selected from the group consisting of:

(a)

wherein R$_1$ is phenyl; tolyl; xylyl; adamantyl; allyl; β-cyanoethyl; fluorenylmethyl; benzyl; benzyl wherein the phenyl ring is substituted with from one to three members selected from halo, nitro, loweralkyl, and loweralkoxy; diisopropylmethyl; diphenylmethyl; cyclohexyl; cyclopentyl; vinyl; t-butyl; t-amyl; dimethyltrifluoromethylmethyl; or dimethylbiphenylmethyl;

(b)

wherein R$_2$ is loweralkyl of two to four carbons or loweralkyl of one to four carbons substituted with from one to five halo groups;

(c)

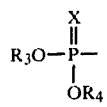

wherein X is S or O and R$_3$ and R$_4$ are each benzyl or loweralkyl;

(d)

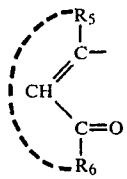

wherein R$_5$ and R$_6$ taken individually are each loweralkyl or R$_5$ and R$_6$ taken together is

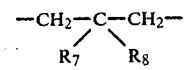

wherein R$_7$ and R$_8$ are each hydrogen or loweralkyl; and (e)

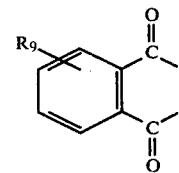

wherein R$_9$ is hydrogen, methyl, halo, or nitro provided that Z is monodentate.

21. The method of claim 20 wherein Z and Z' are the same.

22. The method of claim 21 wherein Z and Z' are each benzyloxycarbonyl or trifluoroacetyl.

23. The method of claim 20 wherein the carboxy activated protected sarcosine formed in step (a) (iii) is a reactive ester of protected sarcosine.

24. The method of claim 20 wherein the protective groups are removed by catalytic hydrogenation in step (b) (ii) and (d).

* * * * *